(12) United States Patent
Hendriks et al.

(10) Patent No.: US 9,733,466 B2
(45) Date of Patent: Aug. 15, 2017

(54) OPTICAL BIOPSY DEVICE

(75) Inventors: Bernardus Hendrikus Wilhelmus Hendriks, Eindhoven (NL); Stein Kuiper, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1291 days.

(21) Appl. No.: 12/593,298

(22) PCT Filed: Mar. 31, 2008

(86) PCT No.: PCT/IB2008/051197
§ 371 (c)(1),
(2), (4) Date: Nov. 17, 2010

(87) PCT Pub. No.: WO2008/120167
PCT Pub. Date: Oct. 9, 2008

(65) Prior Publication Data
US 2011/0054348 A1  Mar. 3, 2011

(30) Foreign Application Priority Data
Mar. 31, 2007 (EP) .................................. 07105417

(51) Int. Cl.
*G02B 23/24* (2006.01)
*G02B 26/10* (2006.01)
(Continued)

(52) U.S. Cl.
CPC ............. *G02B 23/243* (2013.01); *G02B 3/10* (2013.01); *G02B 26/103* (2013.01);
(Continued)

(58) Field of Classification Search
CPC .......... G02B 3/10; G02B 15/00; A61B 5/0068
(Continued)

(56) References Cited

U.S. PATENT DOCUMENTS 3,864,037 A * 2/1975 Johnson .................... G01J 3/02
250/214 VT
4,704,007 A  11/1987 Landre et al.
(Continued)

FOREIGN PATENT DOCUMENTS

CN       1841113 A      10/2006
DE  102005036486 A1     1/2007
(Continued)

OTHER PUBLICATIONS

Laemmel et al: "Fibered Confocal Fluorescence Microscopy (Cell-ViZio) Facilitates Extended Imaging in Thee Field of Microcirculation"; Journal of Vascular Research, 2002, vol. 41, pp. 400-411.

*Primary Examiner* — Sean Dougherty

(57) ABSTRACT

An objective lens system for an optical biopsy device has a lens that comprises a first part configured for viewing at a first magnification, and a second part configured for viewing at a second magnification. The second magnification is substantially different from the first magnification. The first magnification enables viewing a larger area of a target and the second magnification enables viewing the target at a cellular level with high sensitivity and specificity. Combining viewing at two different magnifications in a single objective lens results in a compact optical biopsy device.

8 Claims, 6 Drawing Sheets

(51) Int. Cl.
*A61B 5/00* (2006.01)
*A61B 10/00* (2006.01)
*A61B 17/00* (2006.01)
*G02B 3/00* (2006.01)
*A61B 90/20* (2016.01)
*G02B 3/10* (2006.01)
G02B 3/02 (2006.01)
A61B 90/00 (2016.01)

(52) U.S. Cl.
CPC ........... *A61B 5/0068* (2013.01); *A61B 5/0084* (2013.01); *A61B 10/00* (2013.01); *A61B 90/20* (2016.02); *A61B 90/361* (2016.02); *A61B 2017/00061* (2013.01); *A61B 2090/3616* (2016.02); *G02B 3/0081* (2013.01); *G02B 3/02* (2013.01); *G02B 26/10* (2013.01)

(58) Field of Classification Search
USPC ......... 600/562–572, 168, 176; 359/362, 676, 359/721
See application file for complete search history.

(56) References Cited

U.S. PATENT DOCUMENTS

| | | |
|---|---|---|
| 4,867,546 A | 9/1989 | Nishioka et al. |
| 4,902,115 A | 2/1990 | Takahashi |
| 4,998,973 A * | 3/1991 | Kikuchi ................... A61B 1/05 348/68 |
| 5,103,497 A | 4/1992 | Hicks |
| 5,777,803 A | 7/1998 | Ju et al. |
| 5,978,140 A * | 11/1999 | Maruyama ............ G02B 5/1842 359/565 |
| 6,072,562 A | 6/2000 | Frick |
| 6,124,962 A * | 9/2000 | Kamikubo ............ G02B 26/125 359/205.1 |
| 6,130,785 A * | 10/2000 | Abe ...................... G02B 5/1895 359/570 |
| 6,349,000 B1 * | 2/2002 | Yamagata ............ G02B 5/1895 359/575 |
| 6,450,949 B1 | 9/2002 | Farkas et al. |
| 6,464,355 B1 * | 10/2002 | Gil ........................... G02B 3/08 351/159.74 |
| 6,485,413 B1 | 11/2002 | Boppart et al. |
| 6,500,114 B1 | 12/2002 | Petitto et al. |
| 6,570,840 B1 * | 5/2003 | Wilkinson ............. G11B 7/0079 369/275.4 |
| 6,595,916 B2 | 7/2003 | Minami et al. |
| 6,870,690 B1 * | 3/2005 | Lawson et al. ................ 359/722 |
| 2003/0009086 A1 * | 1/2003 | Black et al. .................. 600/168 |
| 2003/0193875 A1 * | 10/2003 | Rilum ................... G11B 7/0079 369/109.02 |
| 2004/0158129 A1 | 8/2004 | Okada et al. |
| 2005/0052753 A1 | 3/2005 | Kanai |
| 2005/0231822 A1 | 10/2005 | Sato |
| 2006/0171041 A1 * | 8/2006 | Olmstead et al. ............ 359/738 |
| 2007/0017993 A1 | 1/2007 | Sander |
| 2007/0149854 A1 * | 6/2007 | Igarashi ............ A61B 1/00096 600/167 |

FOREIGN PATENT DOCUMENTS

| | | | |
|---|---|---|---|
| WO | 2004027489 A1 | 4/2004 | |
| WO | WO 2006/035362 * | 4/2006 | ............... G11B 7/00 |
| WO | 2007108257 A1 | 9/2007 | |

* cited by examiner

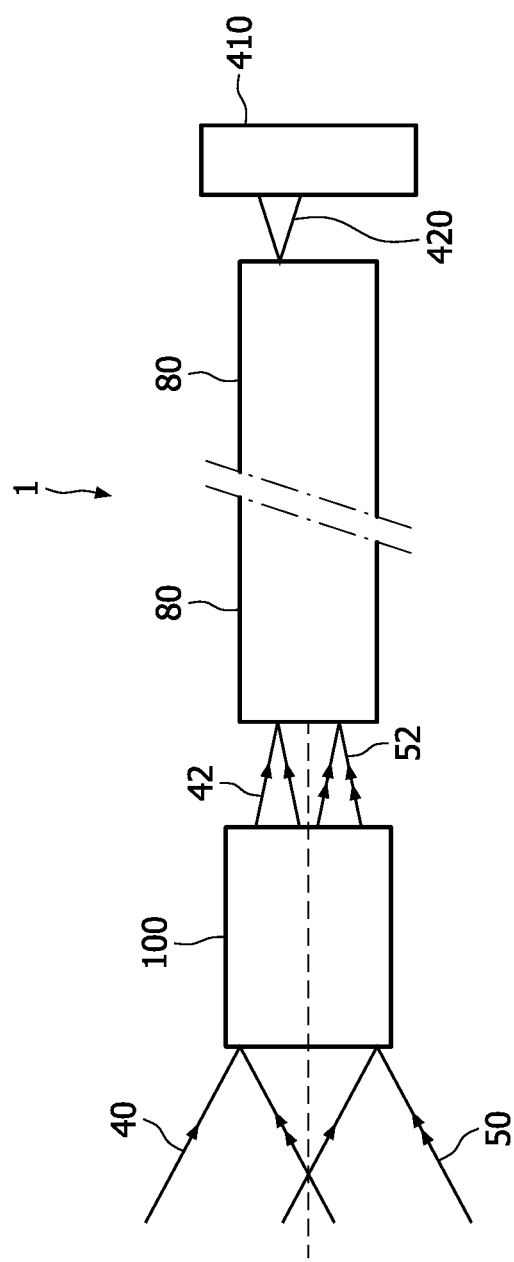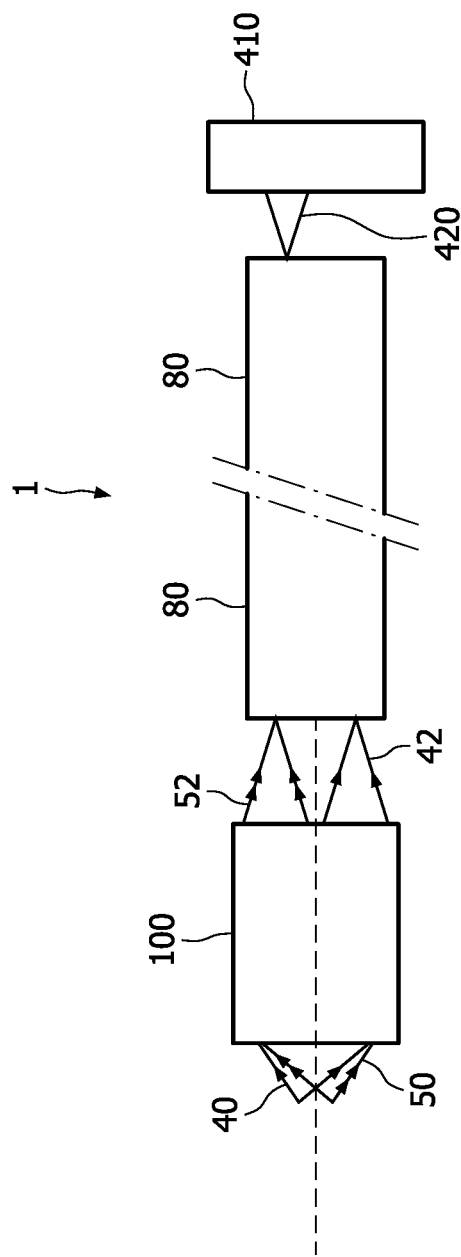

OPTICAL BIOPSY DEVICE

FIELD OF THE INVENTION

This invention relates to an optical biopsy device, more in particular to an objective lens included in the optical biopsy device.

BACKGROUND TO THE INVENTION

A biopsy is carried out during a minimal-invasive surgery to determine the status of a suspicious lesion. Since the suspicious lesions must be visible for a surgeon, these biopsies are taken generally in a later stage of a disease. The biopsies are then sent to a pathologist to investigate target tissue sections. The outcome thus depends on the local tissue samples that could or could not represent the actual disease stage in the tissue. Optical biopsy is an alternative method, where in-vivo optical technology is used to determine whether the disease has affected the tissue. This method also enables the diagnosis of the disease in an early stage. Light can interact with the tissue in a number of ways, including elastic and inelastic (multiple or single) scattering, reflection of boundary layers and absorption, and can for instance lead to fluorescence and Raman scattering. All of these can be utilized to measure any abnormal change in the tissue. This is beneficial to a patient, because no tissue is removed and an analysis can be performed in real time on the spot at all necessary locations. Furthermore automatic diagnosis would save a lot of time for the patient as well as for the surgeon who can diagnose and treat the person instead of waiting for pathology results.

An optical biopsy device must fulfill two requirements to be useful. Firstly it must be able to scan a significant area within a limited time. Secondly, it must have a high sensitivity and specificity. Currently, various optical methods have been proposed for cancer detection. The methods, capable of screening larger areas (in general non-point-like methods) that are available, have high sensitivity but have a rather low specificity. Hence these methods produce a lot of false positives. Methods that have a much higher specificity are in general point like measuring methods. These methods can give a good diagnosis but are not suited to scan significant areas in a short period of time. To fulfill both the above-mentioned requirements, two different optical devices are required. One based on a "camera" like of imaging capable of viewing larger areas and another one based on a "microscope" like imaging capable of viewing tissue on a cellular level. It is apparent that the biopsy procedures would be more efficient and effective if a single optical biopsy device can switch between two different views of a target site without removing the device from the patient.

Although combining a camera and a microscope functions in one device have been described in patent application US20040158129, the two optical modalities are still separate entities placed aside of each other. This results in rather bulky devices. Since for minimal invasive procedures the width of the device is of utmost importance, such solutions as described in US20040158129 may not be preferable.

It would therefore be advantageous to have an optical biopsy device which does not have the disadvantage that is described above and more in particular to have a compact optical biopsy device that enables camera like (macroscopic) and microscope like imaging possible.

Particular and preferred aspects of the invention are set out in the accompanying independent and dependent claims. Features from the dependent claims may be combined with features of the independent claims and with features of other dependent claims as appropriate and not merely as explicitly set out in the claims.

SUMMARY OF THE INVENTION

According to a first aspect of the invention, an objective lens system for an optical biopsy device has a lens comprising a first part configured for viewing at a first magnification, and a second part configured for viewing at a second magnification, wherein the second magnification is substantially different from the first magnification. The first magnification allows viewing a significant area of a target being imaged whereas the second magnification allows viewing the target with a high sensitivity and specificity. For minimal invasive procedures, it is critical to have a compact optical biopsy device. Combining viewing at two different magnifications in a single objective lens system significantly reduces the width of the biopsy device and also enables viewing larger areas with higher specificity.

According to an embodiment of the invention, the first part and second part of the lens are concentric to each other and the second part substantially surrounds the first part. The first part is configured to form an image at the first magnification and the second part is configured to form the image at the second magnification.

According to yet another embodiment of the invention, the first part has a first curvature and the second part has a second curvature. The first curvature is substantially different from the second curvature.

According to another embodiment of the invention, $$\left|\frac{c_2 - c_1}{c_1}\right| > 0.05$$

wherein $c_1$ is the curvature of the first part and $c_2$ is the curvature of the second part. This ratio ensures that the first magnification is substantially different from the second magnification.

According to a further embodiment of the invention, the first curvature and the second curvature have different signs. Such a configuration allows a high ratio of second and first magnifications.

According to a further embodiment of the invention, the first magnification is associated with a macroscopic view and the second magnification is associated with a microscopic view. Macroscopic view enables viewing a significant area of a target whereas microscopic view enables viewing the target at a cellular level with high specificity and sensitivity. For an optical biopsy device to be practically useful, a combination of a macroscopic view capable of viewing larger area of the target and a microscopic view capable of viewing the target on a cellular level is important.

According to a still further embodiment of the invention, the first magnification is at least 10 times smaller than the second magnification.

According to still another embodiment of the invention, the first part has a first wavelength sensitive transmission coating and the second part has a second wavelength sensitive transmission coating. Such coatings provide an additional selection means to the objective lens to switch between macroscopic and microscopic views. These coatings are preferably used in combination with two illumination sources of different wavelengths. When illumination is with the first source, the coating on the second part of the lens does not transmit the light of the first source and the first part of the lens forms an image in the first viewing mode. When illumination is with the second source, the coating on the first part of the lens does not transmit the light of the second source and the second part of the lens forms an image in the second viewing mode. Preferably the first viewing mode is the macroscopic viewing mode and the second viewing mode is the microscopic mode.

According to a second aspect of the invention, an optical biopsy device comprises an inserting tube to be inserted into a body, and an objective lens system secured in a tip end of the inserting tube for viewing in vivo tissues within the body at a first magnification and for viewing in vivo tissues within the body at a second magnification. The second magnification is higher than the first magnification. The objective lens system has a first part configured for viewing at the first magnification and a second part configured for viewing at the second magnification. With this kind of an optical biopsy device, the examining physician could scan larger area of the target (macroscopic view) and upon noticing a suspicious region, directly view in situ the single cells (microscopic view) to make a pathological determination during the course of a single optical biopsy procedure.

According to an embodiment of the invention, the optical biopsy device further comprises a diaphragm configured for switching the viewing between the first magnification and the second magnification. The diaphragm preferably consists of an inner part and an outer part. Preferably, in the macroscopic view, the inner part is made transparent and the outer part is made opaque. On the contrary, in the microscopic view, the inner part is made opaque and the outer part is made transparent.

According to another embodiment of the invention, the diaphragm comprises liquid crystal. Incorporating the liquid crystal diaphragm can reduce mechanical moving parts, which are relatively large and expensive to produce.

According to yet another embodiment of the invention, the diaphragm is configured to work on the electro-wetting principle. Such diaphragms are compact and have no mechanical moving parts.

According to a further embodiment of the invention, the optical biopsy device further comprises an image sensor. The objective lens forms an image of the target on the image sensor.

According to a still further embodiment of the invention, the optical biopsy device further comprises a fiber bundler configured for relaying an image formed; and a console optically coupled to the fiber bundler and configured for reading out the image formed. The image sensor is generally integrated into an optical head. To make the design of the optical head simpler, the image can be relayed using the fiber bundler. Instead of imaging onto the image sensor, the target is imaged on one end of a fiber bundler. This fiber bundler consists of many tiny fibers. The image is relayed by this fiber bundler to the other end of the fiber bundler. The other end of the fiber bundler is probed by the beam of a console of the optical biopsy device.

According to another embodiment of the invention, the optical biopsy device further comprises a single scanning fiber configured for reading out an image formed; and a console optically coupled to the single scanning fiber configured for reconstructing the image formed.

BRIEF DESCRIPTION OF THE FIGURES

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

FIG. 4a shows an optical biopsy device according to an embodiment of the invention, where an image is formed in a macroscopic view and an image sensor is replaced by a fiber bundler;

FIG. 4b shows an optical biopsy device according to an embodiment of the invention, where an image is formed in a microscopic view and an image sensor is replaced by a fiber bundler;

DETAILED DESCRIPTION OF THE INVENTION

Figure 1:
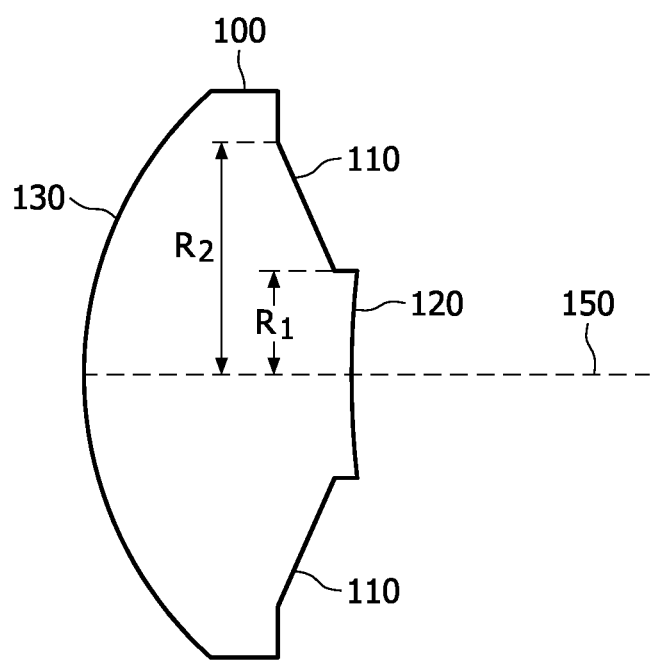
FIG. 1 shows an objective lens system according an embodiment of the invention.

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

In the context of the invention, target can be any interior region including lung, bladder, abdominal cavity, knee joint and the like. The examining physician could examine the interior region and upon noticing a suspicious region i.e. a lesion, he can view in situ the single cells of the lesion. In the same context, macroscopic view refers to viewing a larger area of the target and microscopic viewing refers to viewing the target at a cellular level with high sensitivity.

FIG. 1 shows an objective lens system 100 with an optical axis 150 according to the invention. It consists of one lens as shown in this example. The lens 100 has a first part 120 with an aperture radius $R_1$ and a second part 110 with an aperture radius $R_2$. The first part 120 of the lens surface is used to form the image of a target being imaged in a macroscopic view and the second part 110 is used to form the image of the target in a microscopic view. Surface 130 is the rotational symmetric aspherical surface of the objective lens 100.

Figure 2A:
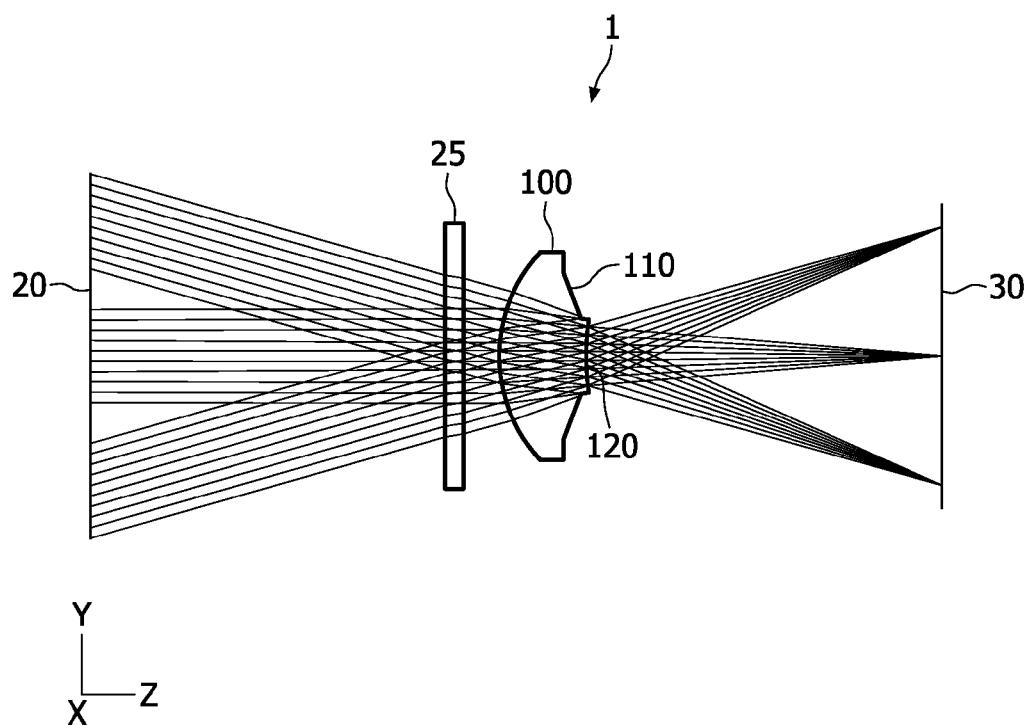
FIG. 2a shows a ray trace of an image formed in a macroscopic view.
Figure 2B:
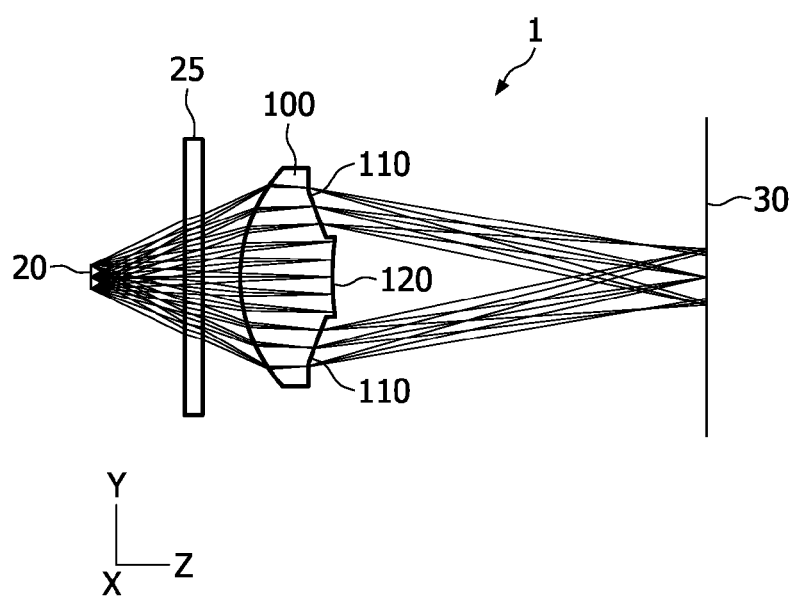
FIG. 2b shows a ray trace of an image formed in a microscopic view.

FIG. 2a shows a ray trace plot showing the macroscopic view of a target (not shown) placed at an object plane 20 where the first part 120 of the objective lens system 100 is used. FIG. 2b shows a ray trace plot showing the microscopic view of the target where the second part 110 of the objective lens system 100 is used. The image is formed on an image sensor 30. A protective glass plate 25 is placed before the objective lens 100.

Figure 3:
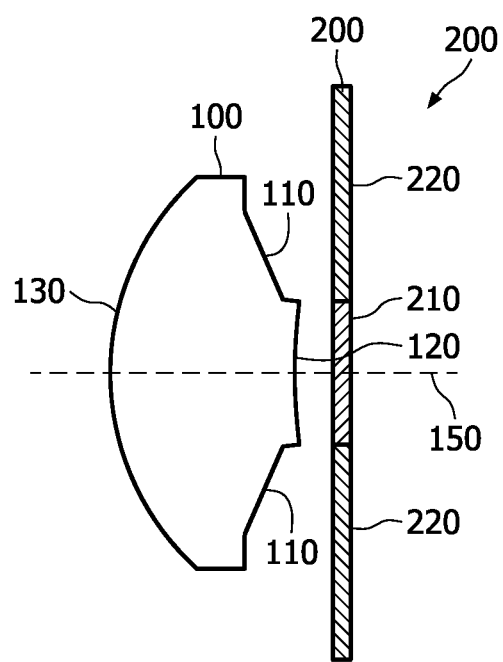
FIG. 3 shows an objective lens with a switchable diaphragm according to an embodiment of the invention.

FIG. 3 shows an objective lens system 100 with an optical axis 150 and a switchable diaphragm 200. The diaphragm consists of two parts: an inner part 210 and an outer part 220. Each of these parts can be switched to a transparent state or to a light absorbing state.

FIGS. 4a and 4b show an optical biopsy device 1 including an objective lens system 100, where an image sensor is replaced by a fiber bundler 80. The objective lens system 100 transforms a beam 40, 50 emerging from a target (not shown) into a beam 42, 52 and forms an image onto one end of the fiber bundler 80. The image is relayed to the other end of the fiber bundler 80 and is probed by the beam 420 of a console 410.

Figure 5:
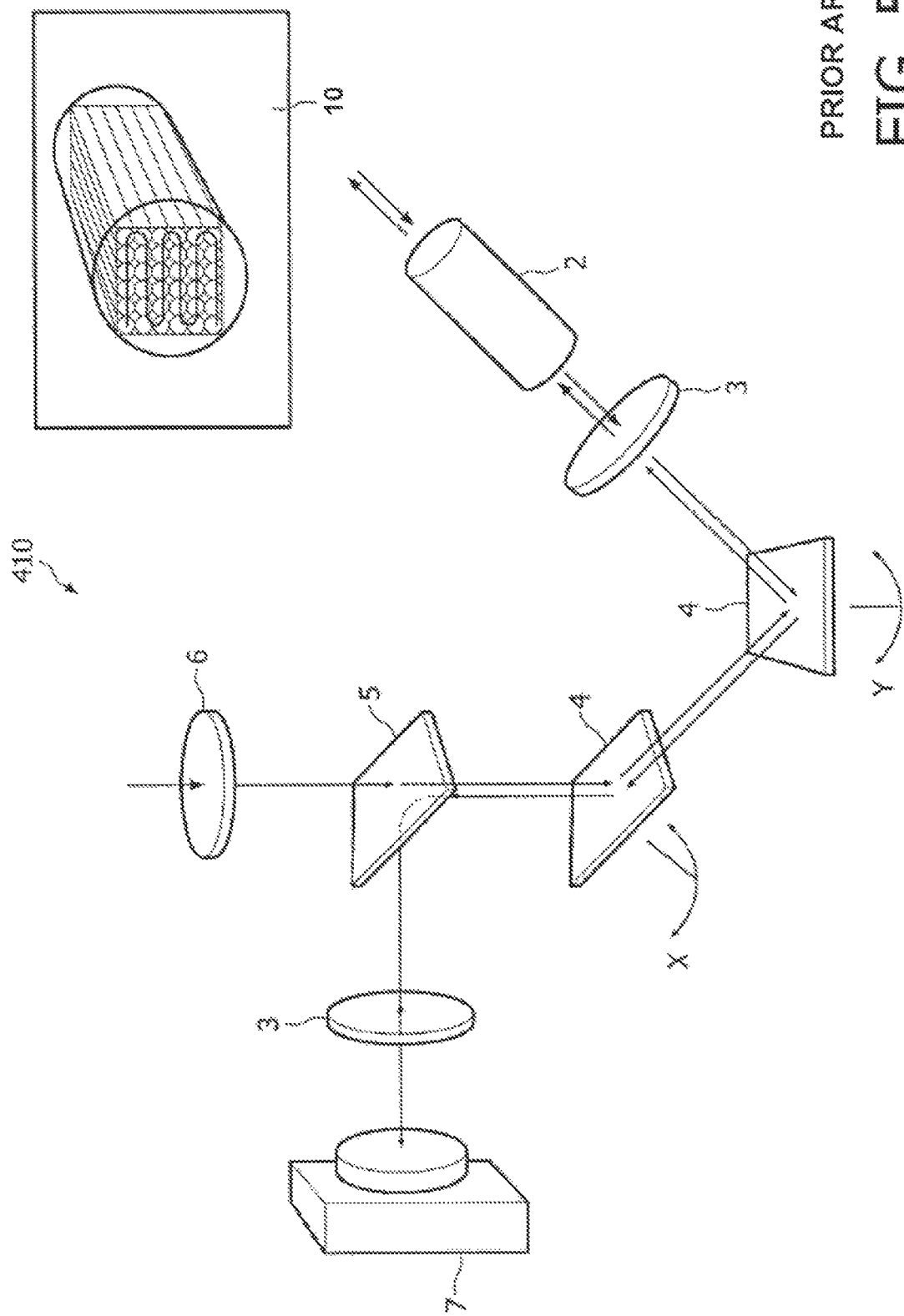
FIG. 5 shows a schematic of a confocal scanning mechanism.

FIG. 5 shows a confocal scanning system as described in J. Vasc. Res. 2004; 41:400-411 by E. Laemmel et al. 1 is a tissue sample. 2 is an image bundler. 3 is a lens. 4 is a tilting mirror. 5 is a dichroic filter. 6 is a laser source. 7 is a photo detector.

FIG. 6 shows an optical biopsy device 1 including an objective lens system 100 where the image sensor is replaced by a scanning fiber 500 that reads out the images. This fiber 500 is connected to a console (not shown). The objective lens system 100 transforms a beam 40, 50 emerging from a target (not shown) into a beam 42, 52. By scanning the fiber end 510, the image formed can be readout and transferred to the console.

As shown in FIG. 1, the objective lens system 100 comprises two parts 120 and 110. The first part 120 of the surface has a best-fit curvature $c_1$ of the best-fit sphere of that part of the surface and the second part 110 of the surface has a best-fit curvature $c_2$ of the best-fit sphere of that part of the surface. $c_1$ and $c_2$ are substantially different.

The rotational symmetric aspherical surface 130 is given by the equation $$z(r) = \frac{cr^2}{1+\sqrt{1-c^2r^2}} + \sum_{i=2}^{5} B_{2i}r^{2i} \quad (1)$$

where z is the position of the surface in the direction of the optical axis 150 in millimeters, r is the distance to the optical axis in millimeters, c is the curvature (the reciprocal of the radius) of the surface and $B_4$ to $B_{10}$ are the coefficients of the i-th power of r. The value of c is 1.096014 mm$^{-1}$. The values of the coefficients $B_4$ to $B_{10}$ are 0.73894797, −8.5560965, 38.136909 and −40.046541, respectively.

The first part 120 of the objective lens system 100 is also described by equation (1) but with the coefficients given by c is 0.5635876 mm$^{-1}$ and the values of the coefficients $B_4$ to $B_{10}$ are 0.6048722, −10.82945, 105.297 and 84.06069 respectively. The point z(0) of this surface lies at 0.5 mm distance along the optical axis from the z(0) point of the surface 130. Furthermore, the aperture radius $R_1$ is 0.2 mm. The second part 110 is also described by equation (1) but with the coefficients given by c is −1.777857 mm$^{-1}$ and the values of the coefficients $B_4$ to $B_{10}$ are 1.122886, 10.22766, −69.06088, and 218.1365, respectively. The point z(0) of this surface lies also at 0.5 mm distance along the optical axis from the z(0) point of the surface 130. Furthermore, the aperture radius $R_2$ is 0.45 mm. The material of the lens has refractive index of 1.581 at 650 nm wavelength and the Abbe number 29.9. The glass plate 25 in front of the lens has a thickness of 0.1 mm and refractive index of 1.515 at a wavelength of 650 nm and the Abbe number is 64.2.

To determine the best-fit radii of the first part 120 and second part 110, the best-fit sphere approach is used. The best-fit sphere is determined by finding the radius of the sphere that minimizes the root-means-square (RMS) deviation between the surface sag and the sag of the best-fit sphere. For the first part 120, the best-fit sphere radius is 1.695 mm. For the second part 110, the best-fit radius is −0.813 mm. A positive radius means that the center of the sphere lies to the right of the surface and a negative sign means that the center of the sphere lies to the left of the surface. The reciprocal of these best-fit radii are then the best-fit curvatures of the surfaces. For the first part 120, the best-fit curvature $c_1$ is then 0.590 mm$^{-1}$ and for the second part 110, $c_2$ is −1.230 mm$^{-1}$. A preferable criterion to define the difference between $c_1$ and $c_2$ is that the mod of the ratio of $(c_2-c_1)$ to $c_1$ should be greater than 0.05

$$\left|\frac{c_2-c_1}{c_1}\right| > 0.05$$

It is further preferable if $$\frac{c_2}{c_1} < 0$$

i.e., the curvatures of first and second part should have different signs.

In the above example the target in the macroscopic view is positioned at 50.5 mm distance from the protective glass plate 25, while the image sensor is at a distance of 2.0 mm from the objective lens system 100. The magnification in this configuration is 0.054. In the microscopic view, the object is positioned at a distance of 0.5 mm from the protective glass plate 25. The magnification is 2.248. The magnification factor between the two modes is 41.6. In general it is preferable that the magnification factor between the two modes is larger than 10. It would be further advantageous to have a magnification factor as high as 40.

The first part 120 and the second part 110 of the objective lens system 100 are preferably coated with two different coatings that are sensitive to different wavelengths to form images in both macroscopic and microscopic modes. Along with these two coatings, two illumination sources with corresponding wavelengths are used. When illumination is with the first source, the coating on the second part of the lens does not transmit the light of the first source and the first part of the lens forms an image in the first viewing mode. When illumination is with the second source, the coating on the first part of the lens does not transmit the light of the second source and the second part of the lens forms an image in the second viewing mode. The ray trace plots in FIGS. 2a and 2b illustrate this.

According to another embodiment as shown in FIG. 3, a switchable diaphragm 200 is used to form images in different modes. The diaphragm consists of two parts: the inner part 210 and the outer part 220. Each of these parts can be switched to a transparent state or to a light absorbing state. In the first viewing mode the inner part 210 is made transparent and the outer part 220 is made opaque. In the second viewing mode the situation is reversed. The opaque part does not transmit light whereas the transparent part forms an image. The diaphragm can be made of liquid crystal diaphragm. Another possibility is to make use of a switchable diaphragm based on the electro-wetting principle as described in EP-A-1543370. The switching can also be based on a liquid crystal principle well known in the liquid crystal based displays.

In all the above-mentioned embodiments, the image is formed on the image sensor 30. To make the design of the optical device simpler, relaying the image using a fiber bundle technique as described for instance in J. Vasc. Res. 2004; 41:400-411 by E. Laemmel et al. is preferably employed. Instead of imaging onto an image sensor 30, it is now imaged on one end of a fiber bundler 80 as shown in FIGS. 4a and 4b. This fiber bundler 80 consists of many tiny fibers. The image is then relayed by this fiber bundler to the other end of the fiber bundler 80. The other end of the fiber can now be probed by the beam 420 of the console 410. An example of such a console 410 is for instance a confocal scanning system as shown in FIG. 5 and as described in J. Vasc. Res. 2004; 41:400-411 by E. Laemmel et al. This reference shows an example of the scanning system 410 and 420 of FIG. 4 to read out the relayed image by the fiber bundler 80.

Figure 6A:
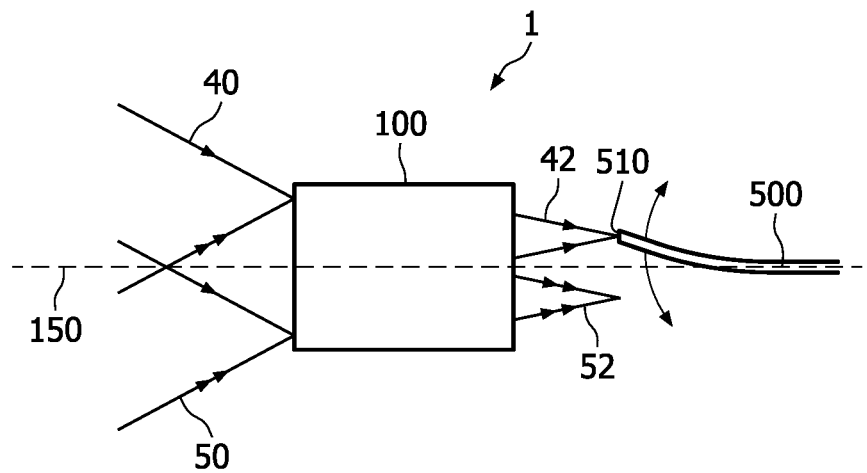
FIG. 6a shows an optical biopsy device where an image sensor is replaced by a scanning fiber that readout the images in a macroscopic view.
Figure 6B:
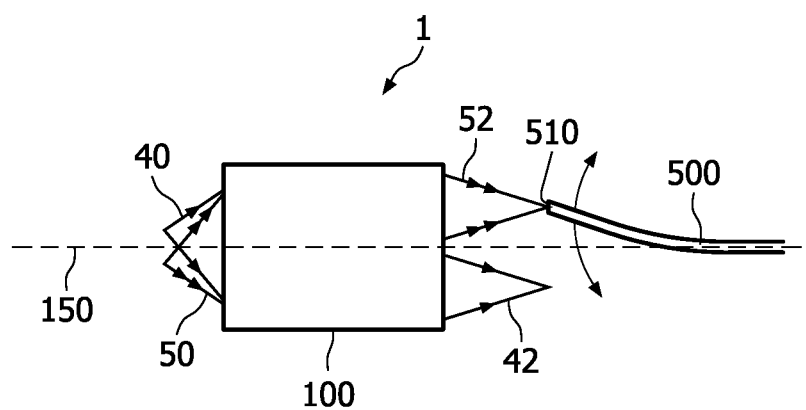
FIG. 6b shows an optical biopsy device where an image sensor is replaced by a scanning fiber that readout the images in a microscopic view.

In a further embodiment, as shown in FIGS. 6a and 6b, a single scanning fiber 500 is used for relaying the image formed. This fiber 500 is connected to a console (not shown). By scanning the fiber end 510, the image formed by the optical probe can be readout and transferred to the console as described in US-A-20050052753.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. An objective lens system for an optical biopsy device having a single lens comprising:
    a first part configured for viewing at a first magnification, the first part having a first curvature,
    a second part configured for viewing at a second magnification, the second part having a second curvature different from the first curvature, wherein the first magnification is associated with a macroscopic view and the second magnification is associated with a microscopic view; and
    a rotational symmetric aspherical surface with a first sag, wherein the first part and the second part of the lens are concentric to each other and the second part substantially surrounds the first part, and
    wherein the rotational symmetric aspherical surface is common to the first part and the second part,
    wherein the first part has a first wavelength sensitive transmission coating that does not transmit any light from a first illumination source, and
    wherein the second part has a second wavelength sensitive transmission coating that does not transmit any light from a second illumination source.

2. The objective lens system of claim 1, wherein the relationship between the first curvature and the second curvature is defined as $$\left|\frac{c_2 - c_1}{c_1}\right| > 0.05$$

wherein $c_1$ is the curvature of the first part and $c_2$ is the curvature of the second part.

3. The objective lens system of claim 1, wherein the first curvature and the second curvature have different signs.

4. The objective lens system of claim 1, wherein the first magnification is at least 10 times smaller than the second magnification.

5. An optical biopsy device comprising:
    an inserting tube to be inserted into a body; and
    an objective lens system secured in a tip end of the inserting tube for viewing at a first magnification and for viewing at a second magnification,
        wherein the objective lens system comprises a single lens with a first part configured for viewing at the first magnification, a second part configured for viewing at the second magnification, and a rotational symmetric aspherical surface,
        wherein the first part and the second part of the lens are concentric to each other and the second part substantially surrounds the first part,
        wherein the rotational symmetric aspherical surface is common to the first part and the second part, and
        wherein the first part has a first curvature and the second part has a second curvature different from the first curvature, and
        wherein the first magnification is associated with a macroscopic view and the second magnification is associated with a microscopic view
    a first illumination source; and
    a second illumination source,
        wherein the first part has a first wavelength sensitive transmission coating that does not transmit any light from the first illumination source and
        the second part has a second wavelength sensitive transmission coating that does not transmit any light from the second illumination source.

6. The optical biopsy device as claimed in claim 5 further comprising an image sensor, wherein the image formed by the lens is relayed on to the image sensor.

7. The optical biopsy device as claimed in claim 5 further comprising: a fiber bundler configured for relaying an image formed by the lens; and a console optically coupled to the fiber bundler and configured for reading out the image formed.

8. The optical biopsy device as claimed in claim 5 further comprising: a single scanning fiber configured for reading out an image formed; and a console optically coupled to the single scanning fiber configured for reconstructing the image formed.

\* \* \* \* \*